United States Patent [19]
Pichon et al.

[11] Patent Number: 6,015,408
[45] Date of Patent: Jan. 18, 2000

[54] APPARATUS FOR IMPACTING BONE CHIPS IN A BONE CANAL

[75] Inventors: Denis Pichon, Bieville-Beuville; John Andrew Storer, Bayeux, both of France

[73] Assignee: Howmedica International Inc., Ireland

[21] Appl. No.: 09/107,270

[22] Filed: Jun. 30, 1998

[30] Foreign Application Priority Data

Jul. 2, 1997 [GB] United Kingdom .................. 9714003

[51] Int. Cl.7 .................................................. A61B 17/56
[52] U.S. Cl. .................................................. 606/53; 606/79
[58] Field of Search .................................. 606/53, 62, 93, 606/99, 105, 102, 95–97; D10/73; 177/246; 128/92; 411/513

[56] References Cited

U.S. PATENT DOCUMENTS

| | | | |
|---|---|---|---|
| D. 391,180 | 2/1998 | Thomas | D10/73 |
| 3,159,226 | 12/1964 | Mittlesteadt | 177/246 |
| 4,341,206 | 7/1982 | Perrett et al. | 128/92 |
| 4,736,738 | 4/1988 | Lipovsek et al. | 128/92 |
| 5,013,318 | 5/1991 | Spranza, III | 606/102 |
| 5,152,792 | 10/1992 | Watkins et al. | 606/87 |
| 5,192,283 | 3/1993 | Ling et al. | 606/93 |
| 5,308,207 | 5/1994 | Jaskowiak | 411/513 |
| 5,470,336 | 11/1995 | Ling et al. | 606/105 |
| 5,509,919 | 4/1996 | Young | 606/80 |
| 5,562,673 | 10/1996 | Koblish et al. | 606/80 |

FOREIGN PATENT DOCUMENTS

| | | |
|---|---|---|
| 0 555 004 A1 | 8/1993 | European Pat. Off. . |
| 0 696 438 A1 | 2/1996 | European Pat. Off. . |
| 0 711 535 A1 | 5/1996 | European Pat. Off. . |

*Primary Examiner*—Michael Buiz
*Assistant Examiner*—Jonathan D. Goldberg
*Attorney, Agent, or Firm*—Lerner, David, Littenberg, Krumholz & Mentlik, LLP

[57] ABSTRACT

An apparatus for impacting bone chips in a bone canal. The impactor has an impaction head of predetermined dimensions and a stem extending therefrom. There is a visual indicator provided with means for secure location on said stem to visually indicate the distance of insertion of the impaction head within a bone canal.

16 Claims, 4 Drawing Sheets

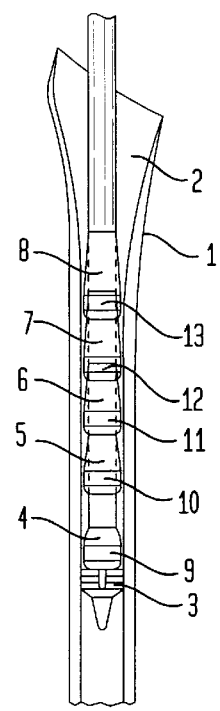
FIG. 1
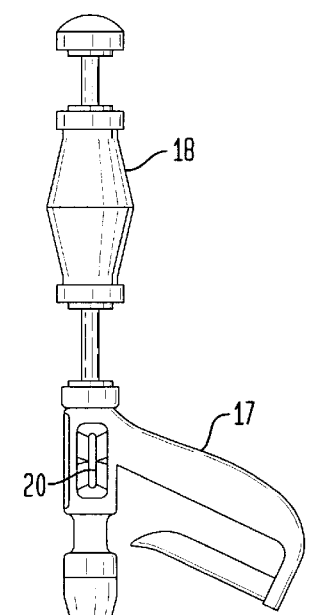
FIG. 2
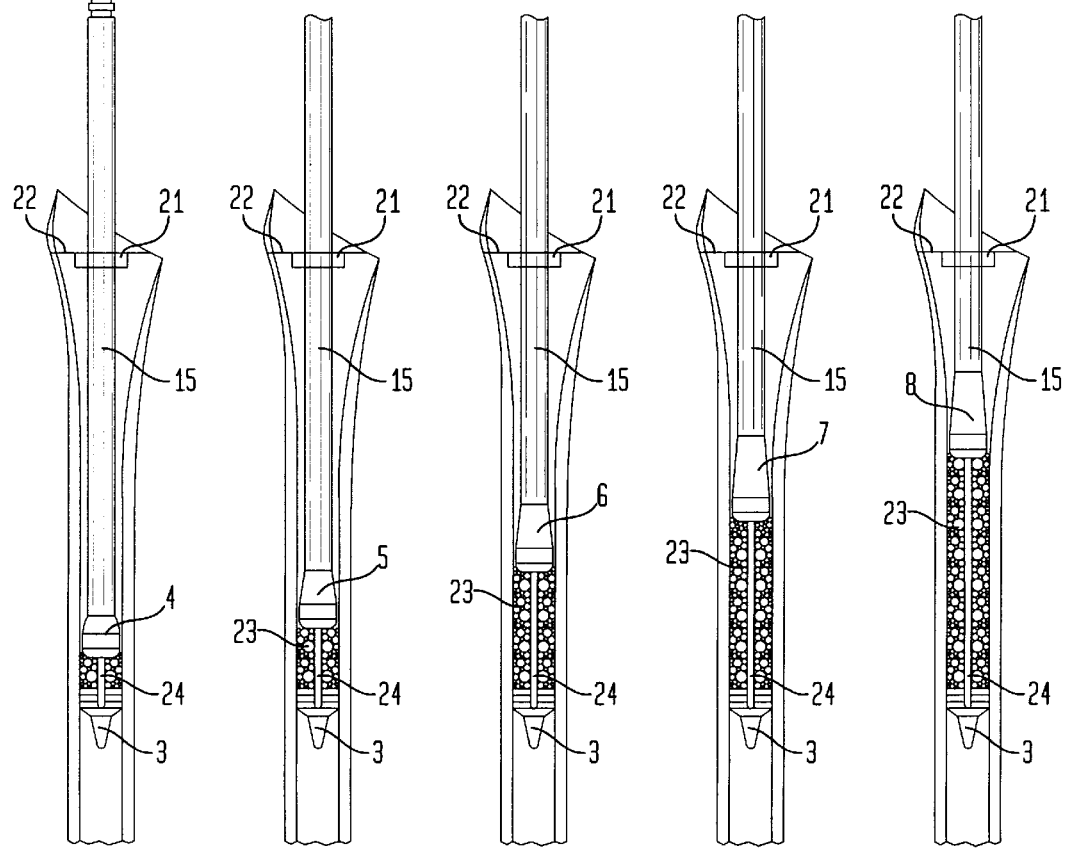

APPARATUS FOR IMPACTING BONE CHIPS IN A BONE CANAL

BACKGROUND OF THE INVENTION

1. Field of the Invention

This invention relates to apparatus for establishing the various sizes of impactor to be used when impacting bone chips in the intramedullary canal of a femur into which the stem of a hip prosthesis is to be located.

2. Description of the Prior Art

The intramedullary canal at the proximal end of a femur is tapered and when a femoral hip prosthesis is to be fitted, the stem is usually reamed out to accept it. In the technique of using bone chips to surround and locate the stem, the bone chips have first to be impacted. Thus, impactors of different shape and diameter have to be used for different parts of the canal. As considerable force is applied to the bone chips to establish them in place, care must be taken to avoid damaging the walls of the intramedullary canal during the impaction technique.

Impactors comprise an impaction head and a stem which can be attached to an impaction tool but before chips are applied, an intramedullary plug is usually passed down the canal to a desired depth. It is important to establish the distance above the bone plug and each size of impactor can be passed without jamming against the wall of the canal. Driving the impactors beyond this point runs the risk of splitting the femur. It is therefore necessary to check that the impactor which corresponds to one size smaller than the intramedullary plug can be passed over a guide wire down to the plug without obstruction, then taking each larger size impactor in turn, passing it over the wire and noting the depth of insertion to which each will go before it jams against the walls of the canal. This can be done by using an impaction tool which is provided with a gauge from which the depth of insertion can be noted. This reading of the appropriate distance above the plug can be noted for each size of impactor. Subsequently, when impacting the bone chips, the impactor must not be driven beyond the noted depth. The plug depth is read off a marked guide wire which extends into the handle of the impactor and can be read through an appropriate viewing window.

As mentioned above, the impaction depth must be noted on a proforma which must then subsequently be consulted for each size of impactor.

Such impactors are shown in U.S. Pat. Nos. 5,192,283 and 5,470,336.

SUMMARY OF THE INVENTION

The present invention is intended to provide apparatus which can be used in this way, but which will be more simple to operate and will not require the use of a listing in a proforma, thus obviating mistakes by the surgeon and the always present danger of damaging or splitting the femur during the impaction technique.

According to the present invention, apparatus for impacting bone chips in a bone canal comprises an impactor having an impaction head of predetermined dimensions and a stem extending therefrom, and a visual indicator provided with means for secure location on the stem to visually indicate the distance of insertion of said impaction head within the bone canal.

Thus, with this apparatus the impactor is first inserted into the bone canal until the impactor head engages or is close to the inner wall thereof. The visual indicator is then securely located on the stem at a predetermined marked position at the proximal end of the bone. When the bone chips are implanted, the impactor head can be driven down compressing the chips until the visual indicator is level with the marking at the proximal end of the bone. This therefore ensures that the impactor is not driven too far down the canal with the likelihood of damage to the bone.

Preferably the visual indicator comprises a clip with means for securing it in position on the stem. It will be appreciated that the clip must be secure so that it does not dislodge during the impaction technique. Thus, when a surgeon has to impact bone chips into, for example, the intramedullary canal of a femur, a bone plug is first inserted and an impactor which is one size smaller than the intramedullary plug size or diameter is passed down the canal and a clip applied, the position of the clip in relation to the proximal end of the canal being marked on the canal appropriately. A series of impactors of different sizes is then passed down the canal, the position of their contact with the canal wall being noted and a clip applied at the appropriate point in relation to the marking.

The surgeon is now armed with a set of impactors which are marked as to the depth to which they should be driven without causing damage and the bone chips are then driven down appropriately using the visual indicator to show when the appropriate impactor has been driven to its safe limit.

The invention therefore also includes a method of impacting bone chips in a bone canal that includes inserting an impactor having a stem and an impaction head of predetermined dimensions into a one canal until the external surface of the impaction head is close to or engages the internal wall of said canal, determining a position at the proximal end of the canal, securely locating a visual indicator on the stem of the impactor to indicate the distance of the impaction head from said determined position, loading said canal with bone chips and impacting said chips with the impaction head until the visual indicator reaches the determined position.

Also included with the invention is a set of parts for impacting bone chips into a bone canal which includes two or more impactors and visual indicators as set forth above and in which the head of each impactor is of different dimensions to the other or others.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 1 is a diagrammatic side view of a femur in section showing the positions of five different impactors in the intramedullary canal;

FIG. 2 is a diagrammatic side elevation showing the positions of five impactors incorporating the present invention in their operative positions in an intramedullary canal and connected to an impaction hammer;

DESCRIPTION OF THE PREFERRED EMBODIMENT

Figure 3:
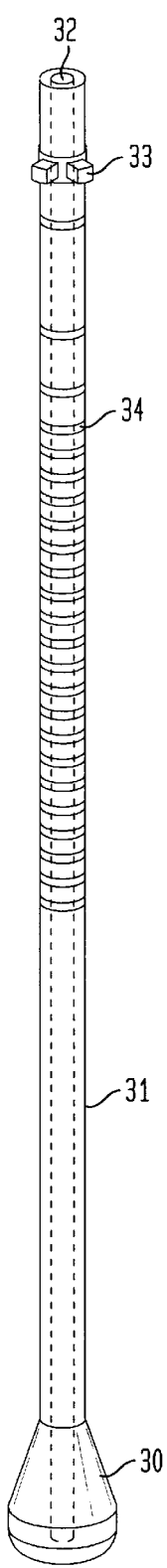
FIG. 3 is a perspective side elevation of part of a first construction of an impactor for use in the invention.
Figure 4:
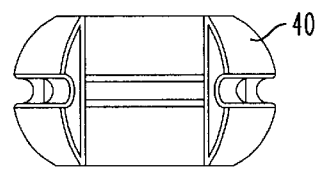
FIG. 4 is an end view of a visual indicator for use with the impactor shown in FIG. 3.
Figure 5:
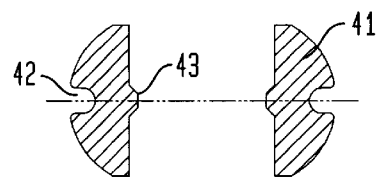
FIG. 5 is a cross-sectional end elevation of the visual indicator shown in FIG. 4.
Figure 6:
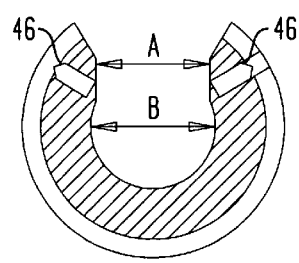
FIG. 6 is a cross-sectional plan view of the visual indicator shown in FIGS. 4 and 5.

As described above, a series of impactors can be used to compress bone chips in the intramedullary canal of, for example, a femur which is to receive the stem of prosthesis. FIG. 1 shows a femur 1 having a tapered intramedullary canal 2. A bone plug 3 is shown in position and the positions of five impactors are indicated by reference numerals 4, 5, 6, 7 and 8. It will be seen that as the diameter of the canal increases towards its proximal end it is necessary to have impactors with heads 9, 10, 11, 12 and 13 of increasing diameter in order to compress bone chips which are applied to the canal above the bone plug 3.

It is essential that the impactor heads are not overdriven into the intramedullary canal 2, otherwise this would cause splitting or damage.

FIG. 2 shows the present invention and how it is operated. Each impactor has a stem 15 and a head 4 to 8 as indicated in FIG. 1. Each of the stems 15 has attachment means 16 to secure it to an impaction tool 17 which carries a slap hammer 18. A guide wire, not shown in FIG. 1, extends from the bone plug 3 through a suitable bore in the impactor and into the impactor tool 17 where it is visible through a window 20. The guide wire can carry markings which will give another visual indication of the depth of movement of the impactor in relation to the bone plug as the impactor moves down the wire and the bone chips are compressed.

The upper part of each of the stems 15 carries a series of parallel circumferential grooves (not shown in FIGS. 1 and 2) onto which a visual indicator provided by a clip 21 can be securely located on the stem. The details of the construction of the impactor stem and the visual indicator are more clearly shown and discussed in FIGS. 3 to 7.

In order to use the invention, the surgeon first inserts the bone plug 3 and threads an impactor 4 which is one size smaller than the bone plug 3. He first inscribes a line marker 22 on the bone and he then fixes the position for the first impactor head 4 and attaches the visual indicator clip 21 to the position shown on the left-hand side of FIG. 2. The surgeon then passes the next size impactor head down the canal until the head is close to or engages the walls thereof and attaches a clip 21 to the stem, repeating the process with impactors having the heads 6, 7 and 8. The surgeon now has a set of impactors which can be safely used by driving them down until the visual indicator is level with the marking 22.

The bone chips, indicated by reference numeral 23, are now sequentially placed and rammed into position by the series of impactors. In FIG. 2 the guide wire is shown by reference numeral 24.

FIG. 3 shows a compactor according to the invention which comprises an impaction head 30, a stem or rod 31 and has a bore 32 to receive a guide wire. The upper end of the stem has a configuration 33 for attachment to an impactor device, for example, of the kind shown in FIG. 2, and the other part of the stem carries a series of parallel circumferential grooves 34.

Figure 7:
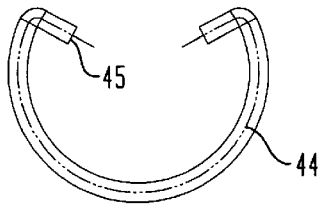
FIG. 7 is a plan view of a metal x-ray for use in the visual indicator.

The visual indicator device according to the invention in this embodiment is in the form of a clip 40 which is made up from a plastics material, for example, polypropylene. In the preferred embodiment clip 40 has a body 41 in the form of an open ring, the outer circumference of which carries a groove 42. The inner circumference of the clip is provided with a protruding engagement flange 43 and the diameter across the inner wall at the position of the flange 43 is such that the clip is a push fit onto the stem 31 when the flange 43 enters one of the grooves 34. The clip body 41 is surrounded by a metal x-ray marker 44, as shown in FIG. 7, and the in-turned ends 45 of the member engage in angled lined bores 46 so that the marker is retained in position. The width across the mouth of the open ring, indicated by reference numeral A, is slightly less than the diameter B of the circular portion of the inner wall so that even without the marker 44, the plastic body 41 is a push fit onto the stem and the push fit is too tight for the clip to be removed manually once it has been put in position on the stem.

In an alternative construction (not shown) the clip 40 can be made from a nylon material or other plastics which can be injection molded and which incorporates a radio opaque material within the molding. Thus, the marker 44 is not required.

Figure 8:
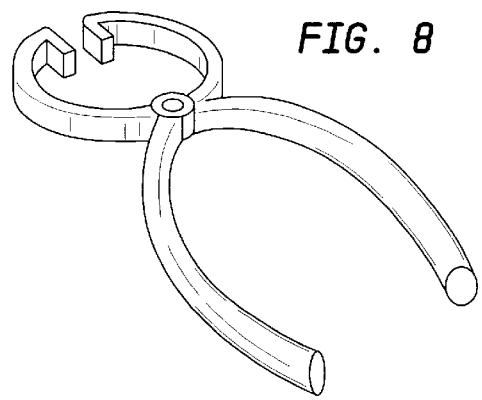
FIG. 8 is an isometric diagrammatic view of a pair of spreader pliers for use in attaching the indicator to the impactor.

FIG. 8 shows a typical pair of pliers which can be used to engage the ends of the opening in the open clip to pull it apart to assist in locating it in position and/or removal from the stem.

Figure 9:
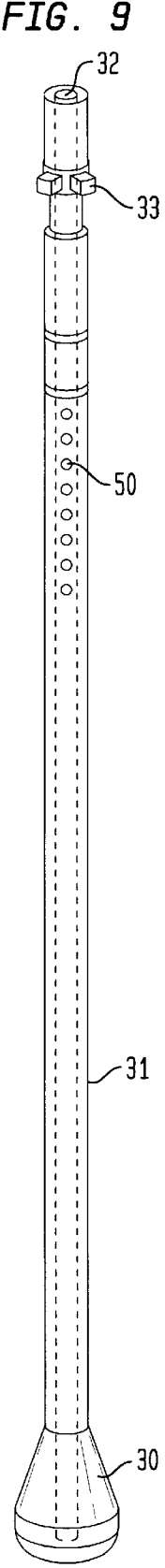
FIG. 9 is a perspective side elevation of part of a second construction according to the invention.
Figure 10:
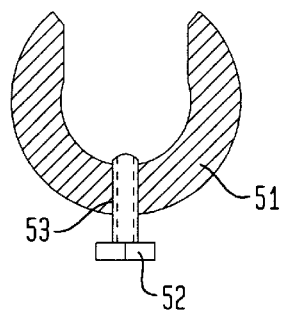
FIG. 10 is a cross-sectional plan view of the visual indicator for use with the construction shown in FIG. 9.

FIGS. 9 and 10 show a second construction of the invention in which the same reference numerals are used to indicate similar parts to those shown in FIGS. 1 to 8.

In this arrangement the stem 31 of the compactor is provided with a continuous series of dimples 50 which extend along its length and only some of which are shown. The dimples are intended to cooperate with a clip 51 which is of substantially the same shape as the clip 40 in the earlier embodiment but does not include the metal X-ray marker 44. This clip is made from a plastics material which has been injection molded and which incorporates a radio opaque material. The clip 51 carries a locking screw 52 located in a threaded opening 53. With this arrangement the clip can be located at any of the longitudinally extending positions provided by the dimples 50 by tightening the screw 52. This visual indicator works in a similar manner to that described in the previous embodiment.

Figure 11:
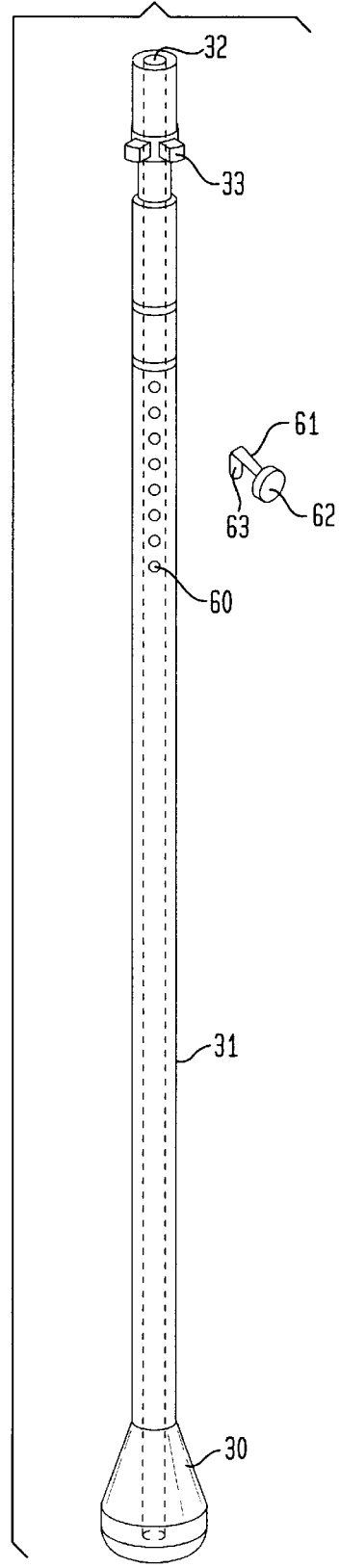
FIG. 11 is a perspective side view of a third construction.

FIG. 11 shows another alternative construction in which once again the same reference numerals are used to indicate similar parts on the impaction stem 31, but in this arrangement a series of spaced apart openings 60 are provided and which are dimensioned to receive a pin 61 which has a head 62 and a drop end link 63. In order to mark the required position it is merely necessary to push the pin through the desired opening 60 and the drop end 63 will ensure that it cannot be inadvertently removed.

Figure 12:
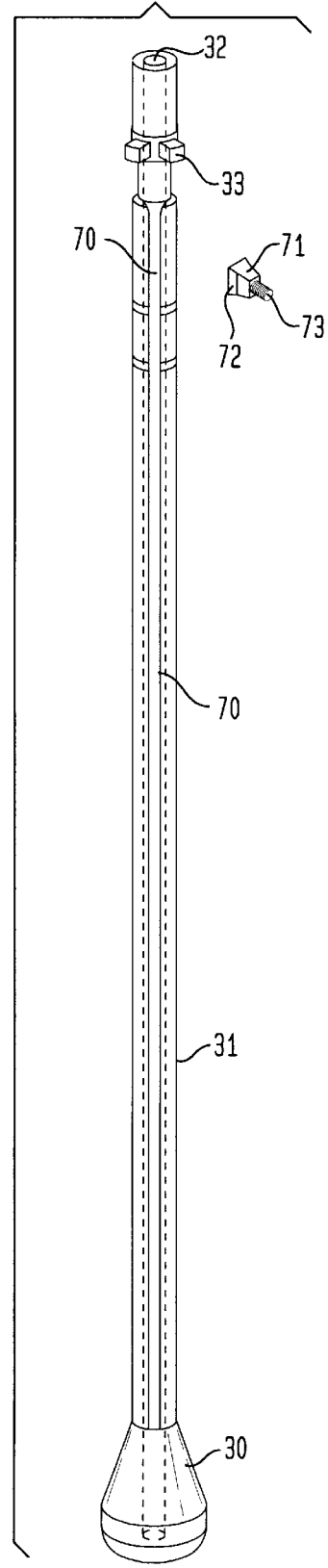
FIG. 12 is a perspective side view of a fourth construction.

FIG. 12 shows yet another construction in which a longitudinally extending dovetail slot 70 is provided and which is shaped to receive a dovetail ended marker 71. The inner end 72 of the marker is shaped to slide in the slot in a longitudinal direction but so that it cannot be removed radially and it can be located in any longitudinal position on the stem 31 by screwing in a lock screw 73 which passes through the marker and engages the inner surface of the slot 70.

Figure 13:
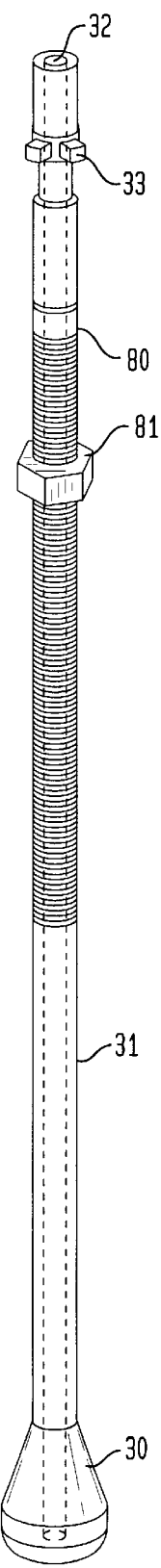
FIG. 13 is a perspective side view of a fifth construction.

FIG. 13 shows another alternate construction in which the stem 31 is provided with a screw thread 80 on which is located a rotatable nut 81. Thus the nut can be moved up and down the screw thread by rotation and a suitable thread or dimensions of the threads on the nut and stem are arranged so that the nut does not turn freely. Thus it can be moved up and down the rod but will remain in position to indicate a desired position. If desired, two nuts could be provided, one acting as a lock nut.

It will be appreciated that the invention provides a considerable advantage over known systems because the visual indicator provides an easy identification of the depth of the impactor when it is in use and, moreover, once the visual indicator has been set on the stem of a particular impactor during the first inspection it will not come loose during the impaction process and can be readily seen by the surgeon.

While several examples of the present invention have been described, it is obvious that many changes and modifications may be made thereunto, without departing from the spirit and scope of the invention.

We claim:

1. A kit including an apparatus for impacting bone chips in a bone canal of a bone having a longitudinal axis and having a reference position marked on said bone with respect to said axis, comprising a series of impactors each having an impaction head of predetermined different diametrical dimensions and a stem extending therefrom, and position indicators selectively engagable with each of said stems at a position therealong corresponding to the reference position on the bone.

2. The apparatus as claimed in claim 1 in which said visual indicator comprises a clip with means for securing it in position on the stem.

3. The apparatus as claimed in claim 2 in which said clip is adapted to engage one of a series of grooves provided in said stem.

4. The apparatus as claimed in claim 2 in which said clip is an interference fit onto said stem.

5. The apparatus as claimed in claim 2 in which said clip is secured by a screw locating in a series of openings in said stem.

6. The apparatus as claimed in claim 1 in which said visual indicator is provided by a pin adapted to locate in a series of openings in said stem.

7. The apparatus as claimed in claim 1 in which said visual indicator is provided by a slide which can be locked into a track provided on said stem.

8. The apparatus as claimed in claim 1 in which said visual indicator is a screw threaded member located on a screw thread carried on said stem.

9. A set of parts for impacting bone chips into a bone canal of a bone having a longitudinal axis and having a reference position marked on said bone with respect to said axis comprising an impaction tool and two or more impactors with an impaction head of each impactor being of different diameter, each impactor having a stem with at least two positioning elements formed thereon, each impaction head and stem being cannulated as well as a distal part of said impaction tool and a position indicator removably engageable with each of the positioning elements on said stem at a position therealong corresponding to said reference position on said bone.

10. The apparatus as claimed in claim 9 in which said visual indicator comprises a clip with means for securing it in position on the stem.

11. The apparatus as claimed in claim 9 in which said clip is adapted to engage one of a series of grooves provided in said stem.

12. The apparatus as claimed in claim 9 in which said clip is a push fit onto said stem and is too tight to be manually removed.

13. The apparatus as claimed in claim 9 in which said clip is secured by a screw locating in a series of openings in said stem.

14. The apparatus as claimed in claim 9 in which said visual indicator is provided by a pin adapted to locate in a series of openings in said stem.

15. The apparatus as claimed in claim 9 in which said visual indicator is provided by a slide which can be locked into a track provided on said stem.

16. The apparatus as claimed in claim 9 in which said visual indicator is a screw threaded member located on a screw thread carried on said stem.

* * * * *

UNITED STATES PATENT AND TRADEMARK OFFICE
CERTIFICATE OF CORRECTION

PATENT NO. : 6,015,408
DATED : January 18, 2000
INVENTOR(S) : Pichon et al.

It is certified that error appears in the above-identified patent and that said Letters Patent is hereby corrected as shown below:

Column 5, line 30, after "comprising", insert -- an impaction tool and --.
Column 5, line 32, after "therefrom,", insert -- each impaction head and stem being cannulated as well as a distal part of said impaction tool -- .

Signed and Sealed this

Twenty-seventh Day of February, 2001

Attest:

NICHOLAS P. GODICI

Attesting Officer

Acting Director of the United States Patent and Trademark Office